United States Patent
Standley et al.

(10) Patent No.: US 11,246,842 B2
(45) Date of Patent: Feb. 15, 2022

(54) METHOD AND COMPOSITIONS FOR DISSOLVING OR SOLUBILIZING THERAPEUTIC AGENTS

(71) Applicant: Windgap Medical, Inc., Somerville, MA (US)

(72) Inventors: Adam R. Standley, Cambridge, MA (US); Kaliappanadar Nellaiappan, Lexington, MA (US); Brent A. Buchine, Watertown, MA (US)

(73) Assignee: Windgap Medical, Inc., Watertown, MA (US)

( * ) Notice: Subject to any disclaimer, the term of this patent is extended or adjusted under 35 U.S.C. 154(b) by 0 days.

(21) Appl. No.: 14/975,695

(22) Filed: Dec. 18, 2015

(65) Prior Publication Data

US 2016/0243060 A1    Aug. 25, 2016

Related U.S. Application Data

(60) Provisional application No. 62/094,063, filed on Dec. 18, 2014.

(51) Int. Cl.

| A61K 31/137 | (2006.01) |
|---|---|
| A61K 31/4045 | (2006.01) |
| A61K 31/485 | (2006.01) |
| A61K 38/26 | (2006.01) |
| A61K 9/00 | (2006.01) |
| A61K 9/16 | (2006.01) |
| A61M 5/32 | (2006.01) |
| A61K 9/14 | (2006.01) |
| A61M 5/28 | (2006.01) |

(52) U.S. Cl.
CPC .......... *A61K 31/137* (2013.01); *A61K 9/0019* (2013.01); *A61K 9/143* (2013.01); *A61K 9/145* (2013.01); *A61K 9/1617* (2013.01); *A61K 9/1676* (2013.01); *A61K 31/4045* (2013.01); *A61K 31/485* (2013.01); *A61K 38/26* (2013.01); *A61M 5/3294* (2013.01); *A61M 5/284* (2013.01)

(58) Field of Classification Search
CPC .......................... A61M 5/3294; A61M 5/284
See application file for complete search history.

(56) References Cited

U.S. PATENT DOCUMENTS

| 4,147,767 A | 4/1979 | Yapel |
|---|---|---|
| 4,479,794 A | 10/1984 | Urquhart et al. |
| 4,511,351 A | 4/1985 | Theeuwes |
| 4,755,169 A | 7/1988 | Sarnoff et al. |
| 4,820,286 A | 4/1989 | van der Wal |
| 6,641,561 B1 | 11/2003 | Hill et al. |
| 6,656,150 B2 | 12/2003 | Hill et al. |
| 6,770,052 B2 | 8/2004 | Hill et al. |
| 6,793,646 B1 | 9/2004 | Giambattista et al. |
| 6,953,455 B2 | 10/2005 | Cho et al. |
| 7,323,477 B2 | 1/2008 | Chow et al. |
| 7,449,012 B2 | 11/2008 | Young et al. |
| 7,544,189 B2 | 6/2009 | Griffiths |
| 7,556,614 B2 | 7/2009 | Griffiths et al. |
| 7,608,055 B2 | 10/2009 | Griffiths et al. |
| 7,621,887 B2 | 11/2009 | Griffiths et al. |
| 7,678,073 B2 | 3/2010 | Griffiths et al. |
| 7,749,190 B2 | 7/2010 | Griffiths et al. |
| 7,757,370 B2 | 7/2010 | Griffiths |
| 7,776,015 B2 | 8/2010 | Sadowski et al. |
| 7,794,432 B2 | 9/2010 | Young et al. |
| 7,947,742 B2 | 5/2011 | Batycky et al. |
| 8,048,035 B2 | 11/2011 | Mesa et al. |
| 8,057,427 B2 | 11/2011 | Griffiths et al. |
| 8,092,420 B2 | 1/2012 | Bendek et al. |
| 8,123,719 B2 | 2/2012 | Edwards et al. |
| 8,177,758 B2 | 5/2012 | Brooks, Jr. et al. |
| 8,187,220 B2 | 5/2012 | Griffiths et al. |
| 8,251,947 B2 | 8/2012 | KraMer et al. |
| 8,313,466 B2 | 11/2012 | Edwards et al. |
| 8,496,619 B2 | 7/2013 | Kramer et al. |
| 8,506,526 B2 | 8/2013 | Griffiths et al. |
| 8,568,367 B2 | 10/2013 | Griffiths et al. |
| 8,613,720 B2 | 12/2013 | Bendek et al. |
| 8,632,504 B2 | 1/2014 | Young |
| 8,696,618 B2 | 4/2014 | Kramer et al. |
| 8,770,827 B2 | 7/2014 | Steinmuller et al. |
| 8,870,827 B2 | 10/2014 | Young et al. |
| 8,945,053 B2 | 2/2015 | Vogt et al. |
| 9,364,610 B2 | 6/2016 | KraMer et al. |
| 9,364,611 B2 | 6/2016 | KraMer et al. |
| 9,586,010 B2 | 3/2017 | Mesa et al. |

(Continued)

FOREIGN PATENT DOCUMENTS

| CN | 1634002 A | 7/2005 |
|---|---|---|
| CN | 1827109 A | 9/2006 |
| CN | 101674812 A | 3/2010 |
| CN | 102389403 A | 3/2012 |
| CN | 102497882 A | 6/2012 |
| CN | 102802668 A | 11/2012 |
| CN | 103442695 A | 12/2013 |
| CN | 106061253 A | 10/2016 |
| FR | 2741810 A1 | 6/1997 |
| JP | 2010-526039 A | 7/2010 |
| JP | 2012-528830 A | 11/2012 |
| JP | 2013-500952 A | 1/2013 |
| JP | 2014-523296 A | 9/2014 |

(Continued)

OTHER PUBLICATIONS

International Search Report and Written Opinion for International Application No. PCT/US2014/071324 dated Sep. 2, 2015.

(Continued)

*Primary Examiner* — Robert A Wax
*Assistant Examiner* — William Craigo
(74) *Attorney, Agent, or Firm* — Wolf, Greenfield & Sacks, P.C.

(57) ABSTRACT

The invention provides pharmaceutical compositions comprising a dry medicament. The dry medicaments can be rapidly dissolved, solubilized, and/or reconstituted to deliver to a subject. The present invention provides methods of preparing a medical solution. The medical solution can be prepared from mixing the pharmaceutical composition as described herein with a first liquid.

21 Claims, 10 Drawing Sheets

(56) References Cited

U.S. PATENT DOCUMENTS

| | | |
|---|---|---|
| 2003/0187388 A1 | 10/2003 | Sharon et al. |
| 2004/0076588 A1 | 4/2004 | Batycky et al. |
| 2004/0110781 A1 | 6/2004 | Harmon et al. |
| 2005/0281883 A1 | 12/2005 | Daniloff et al. |
| 2006/0257488 A1* | 11/2006 | Hubbard ............... A61K 9/0024 424/486 |
| 2007/0203247 A1 | 8/2007 | Phillips et al. |
| 2008/0026934 A1 | 1/2008 | Jensen et al. |
| 2008/0269347 A1* | 10/2008 | Bruss .................. A61K 31/135 514/653 |
| 2010/0179090 A1 | 7/2010 | Havelund et al. |
| 2011/0092906 A1 | 4/2011 | Bottger et al. |
| 2011/0092917 A1 | 4/2011 | Wei et al. |
| 2012/0016296 A1 | 1/2012 | Charles |
| 2012/0046225 A1 | 2/2012 | Prestrelski et al. |
| 2012/0130318 A1 | 5/2012 | Young |
| 2013/0018313 A1 | 7/2013 | Dede |
| 2013/0178823 A1* | 7/2013 | Buchine ................ A61J 1/2093 604/506 |
| 2014/0088512 A1 | 3/2014 | Quinn |
| 2014/0276385 A1 | 9/2014 | Buchine et al. |
| 2014/0276430 A1 | 9/2014 | Baker et al. |
| 2015/0011975 A1 | 1/2015 | Anderson et al. |
| 2015/0231334 A1 | 8/2015 | Buchine et al. |

FOREIGN PATENT DOCUMENTS

| | | | |
|---|---|---|---|
| WO | WO 00/48662 A1 | 8/2000 | |
| WO | WO 00/66214 A1 | 11/2000 | |
| WO | WO 02/41830 A2 | 5/2002 | |
| WO | WO 03/047663 A2 | 6/2003 | |
| WO | WO 2007/057717 A2 | 5/2007 | |
| WO | WO 2008/132224 A2 | 11/2008 | |
| WO | WO 2010/139751 A2 | 12/2010 | |
| WO | WO 2010/139752 A2 | 12/2010 | |
| WO | WO 2011/012719 A1 | 2/2011 | |
| WO | WO 2012/122535 A2 | 9/2012 | |
| WO | WO 2012/177948 A2 | 12/2012 | |
| WO | WO 2014/026694 A1 | 2/2014 | |
| WO | WO 2014/060563 A2 | 4/2014 | |
| WO | WO 2014059444 A2 * | 4/2014 | .......... A61M 5/2046 |
| WO | WO 2014/066731 A1 | 5/2014 | |
| WO | WO 2014/146060 A1 | 9/2014 | |
| WO | WO 2014/205463 A1 | 12/2014 | |
| WO | WO 2015/095624 A2 | 6/2015 | |
| WO | WO 2019/011069 A1 | 1/2019 | |

OTHER PUBLICATIONS

International Preliminary Report on Patentability for International application No. PCT/US2014/071324 dated Jun. 30, 2016.

International Search Report and Written Opinion for International Application No. PCT/US2015/066940 dated Feb. 25, 2016.

International Preliminary Report on Patentability for International Application No. PCT/US2015/066940 dated Jun. 29, 2017.

Supplementary European Search Report for European Application No. EP 14 872 735.7 dated Aug. 23, 2017.

Supplementary European Search Report for Application EP 15871257.0 dated Jul. 11, 2018.

Bansal, Product Development Issues of Powders for Injection. Pharmaceutical Technology. Mar. 2002; available online Jan. 2002:pp. 122-132. Retrieved from the internet under https://www.researchgate.net/profile/Arvind_Bansal/publication/228912123_Product_development_issues_of_powder_for_injection/links/55e43bc808aecb1a7cc8fa.pdf on Aug. 10, 2018.

Landy et al., An open-label trial of a sumatriptan auto-injector for migraine in patients currently treated with subcutaneous sumatriptan. Headache. Jan. 2013;53(1):118-125. doi: 10.1111/j.1526-4610.2012.02295.x. Epub Nov. 13, 2012.

[No Author Listed], Adrenalin (epinephrine injection) 1 mg/mL (1:1000). JHP Pharmaceuticals, LLC. Dec. 2012. <URL: https://www.accessdata.fda.gov/drugsatfda_docs/label/2012/204200s000lbl.pdf> [retrieved from internet on Mar. 18, 2021] 10 pages.

[No Author Listed], Epinephrine Injection USP, Material Data Sheet. Luitpold Pharmaceuticals, Inc. Jan. 10, 2009. <URL: https://marketing.msdsonline.com/library/ioj/ioj708.pdf > retrieved from internet on Mar. 18, 2021] 8 pages.

Kerddonfak et al., The stability and sterility of epinephrine prefilled syringe. Asian Pac J Allergy Immunol. Mar. 2010;28(1):53-7.

* cited by examiner

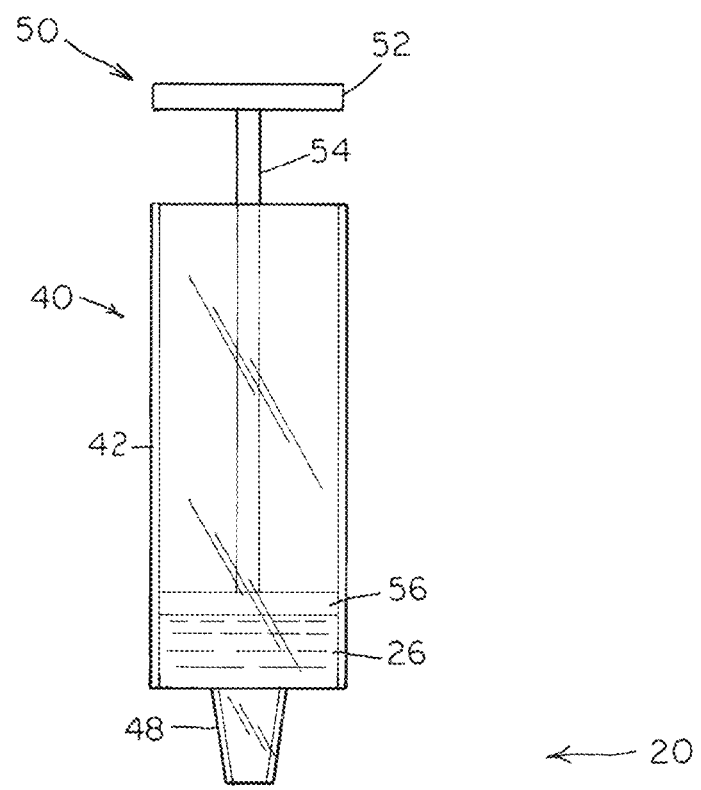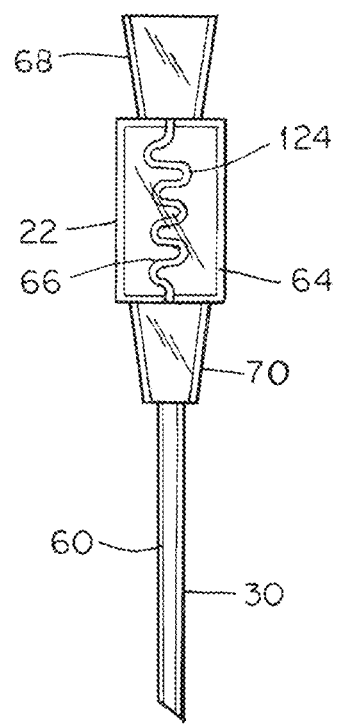
Fig. 2

Table 1.

| Acid (liquid) | | | | |
|---|---|---|---|---|
| Name | Formula | | | Valence |
| | "A" | "B" | | |
| Hydrochloric | H | Cl | hydrochloride | 1 |
| Nitric | H | NO3 | nitrate | 1 |
| Sulfuric | H2 | SO4 | sulfide | 2 |
| Phosphoric | H3 | PO4 | phosphide | 3 |
| Tartaric Acid | H2 | C4H4O6 | tartrate | 2 |
| *Malic Acid* | | | | |
| *Malonic Acid* | | | | |
| *Maleic Acid* | | | | |
| *Fumaric Acid* | | | | |
| *Succinic Acid* | | | | |
| *Formic Acid* | | | | |

Fig. 3

Table. 2

| Organic Salt ion (solid) | | | Organic Salt Anion (solid) | | |
|---|---|---|---|---|---|
| Name | Formula "C" | Valence (+) | Name | Formula "D" | Valence (−) |
| Sodium | Na | 1 | Citrate | C6H5O7 | 3 |
| Calcium | Ca | 1 | Acetate | CH3CO2 | 1 |
| Potassium | K | 1 | Phosphate | PO4 | 3 |
| Ammonium | NH4 | 1 | Sulfate | SO4 | 2 |
| | | | Nitrate | NO3 | 1 |
| | | | Tartrate | | |
| | | | Succinate | | |
| | | | Malate | C4H4O5 | 2 |
| | | | Maleate | C4H4O4 | |

Fig. 4

Table. 3

| Medication (solid) Name "Rx" | Medication Salts (some examples) |
|---|---|
| Epinephrine | Epinephrine Hydrochloride |
| Glucagon | Epinephrine Bitartrate |
| Sumatriptan | Glucagon Hydrochloride |
| | Glucagon Nitrate |
| | Sumatriptan Hydrochloride |
| | Sumatriptan Succinate |
| | Morphine hydrochloride |
| | Morphine Sulfate |

Fig. 5

Table 4.

| Type | Acid | | Conjugate Salt | | Medication (freebase) | Medication (salt form) | | Exchange Salt | | Weak Acid |
|---|---|---|---|---|---|---|---|---|---|---|
| 1 | A-B | + | C-D | + | Rx → | Rx*A-B | + | C-B | + | A-D |
| 2 | A-B | + | C-D | + | Rx → | Rx*B | + | C-B | + | A-D |
| 3 | A-B | + | C-D | + | Rx → | Rx*D | + | C-B | + | A-D |
| 4 | A-B | + | C-D | + | Rx → | Rx*A-B + Rx*D @equilibrium | + | C-B | + | A-D |
| 5 | A-B | + | C-D | + | Rx → | Rx*B + Rx*D @equilibrium | + | C-B | + | A-D |

Fig. 6

Table 5.

Reaction Examples (Type 1)

| Acid/Base | | Organic Ion | Organic Anion | Medi-cation | Medi-cation | Acid/Base (salt) | | Exchange Salt | | Weak Acid | | Organic Salt Excess (if any) | | Acid Excess (if any) |
|---|---|---|---|---|---|---|---|---|---|---|---|---|---|---|
| A | B | C | D | E | E | A | B | C | B | A | D | D | | |
| H | Cl | Na | Citrate | Epi.→ | Epi. | H | Cl | Na | Cl | H | Citrate | Citrate Na | Citrate | H |
| 4 | 4 | 3 | 1 | 1 | 1 | 1 | 1 | 3 | 3 | 3 | 1 | 1 | | |
| 4 | | 1 | | 1 | 1 | | | 3 | | 1 | | | | |
| H | Cl | Na | Acetate | Epi.→ | Epi. | H | Cl | Na | Cl | H | Acetate | Acetate Na | Acetate | H |
| 3 | 3 | 2 | 2 | 1 | 1 | 1 | 1 | 2 | 2 | 2 | 2 | 2 | | |
| 3 | | 2 | | 1 | 1 | | | 2 | | 2 | | | | |

Reaction Examples (Type 5)

| Acid/Base | | Organic Ion | Organic Anion | Medi-cation | Medi-cation | Acid/Base (salt) | | Exchange Salt | | Weak Acid | | Organic Salt Excess (if any) | | Acid Excess (if any) |
|---|---|---|---|---|---|---|---|---|---|---|---|---|---|---|
| A | B | C | D | E | E | A | B | C | B | A | D | D | | |
| H | Cl | Na | tartrate | Epi.→ | Epi. bitartrate + Epi. HCl | H | Cl | Rx*B | Cl | H | tartrate | tartrate Na | tartrate | H |

Fig. 7

Type 1 Reaction

4 HCl + Na₃C₆H₅O₇ + C₉H₁₃NO₃ → C₉H₁₃NO₃·HCl + 3 NaCl + C₆H₈O₇

3 HCl + 2 C₂H₃NaO₂ + C₉H₁₃NO₃ → C₉H₁₃NO₃·HCl + 2 NaCl + 2 C₂H₄O₂

Type 5 Reaction

3 HCl + Na₂C₄H₄O₆ + 2 C₉H₁₃NO₃ → C₉H₁₃NO₃·HCl + C₉H₁₃NO₃·C₄H₆O₆ + 2 NaCl

Fig. 8

METHOD AND COMPOSITIONS FOR DISSOLVING OR SOLUBILIZING THERAPEUTIC AGENTS

RELATED APPLICATIONS

The present invention claims priority under 35 U.S.C. § 119(e) to U.S. Provisional patent application U.S. Ser. No. 62/094,063, filed Dec. 18, 2014, the entire contents of which is incorporated herein by reference.

BACKGROUND OF INVENTION

Individuals who suffer from certain medical conditions are often required to keep an auto-injector or prefilled syringe nearby in order to address a medical need. A few examples of this are insulin pens for people with diabetes, epinephrine autoinjectors for those with food and insect stings allergies, and antidotes for soldiers at risk of exposure to chemical and/or biological toxins in the field.

Exposure to certain substances, such as, for example, peanuts, shellfish, bee venom, certain drugs, toxins, and the like, can cause allergic reactions in sensitive individuals. Such allergic reactions can lead to anaphylactic shock. This can cause a sharp drop in blood pressure, hives, and/or severe airway constriction and can be a life-threatening condition. The response of a sensitive individual to an allergen can either gradually or abruptly increase or decrease over time, making a large portion of those sensitive individuals needful of a solution to mitigate the effects of anaphylactic shock. Responding rapidly to mitigate the effects from such exposures can prevent injury and/or death. For example, in certain situations, an injection of epinephrine (i.e., adrenaline) can provide substantial and/or complete relief from the allergic reaction.

With regards to allergies, for example, an allergic reaction may occur in a location physically distant from the nearest hospital or medical facility. For example, bee stings are more likely to occur outside than indoors. Food containing peanuts are more likely to be supplied to the individual away from a controlled home environment like at a baseball park.

Because emergency medical facilities may not be available when an individual is suffering from an allergic reaction, some individuals carry a medicament delivery device, such as, for example, an auto-injector, to rapidly self-administer the epinephrine in response to an allergic reaction. Having an epinephrine auto-injector nearby enables emergency intervention after an exposure to an allergen to reduce and/or reverse the side-effects of life threatening anaphylaxis.

For patients that are required to carry epinephrine auto-injectors with them, the thermal stability profile of the medication can present an issue. Patients must care for their medications in a way that prevents them from being exposed to excessive heat or cold outside of controlled room temperature. Not doing so can degrade the medication rapidly and result in a drug that doesn't have the recommended potency to deal with the onsets of anaphylactic shock.

SUMMARY

The invention provides dry pharmaceutical compositions (e.g., dry powder compositions) that can be rapidly reconstituted into solutions for delivery to a subject, for example a human subject (e.g., by injection). In some embodiments, a dry pharmaceutical composition comprises a combination of a dry medicament and one or more dry pH adjusting agents. In some embodiments, a dry pharmaceutical composition can be reconstituted into a solution by mixing with a first solution. In some embodiments, the first solution has a pH that rapidly dissolves the dry medicament. In some embodiments, the dry pH adjusting agent dissolves less rapidly than the dry medicament, resulting in a pH adjustment of the solution after dissolution of the dry medicament. Aspects of the disclosure are useful to promote rapid dissolution of a dry medicament (e.g., epinephrine) at a pH that may not be physiologically acceptable followed by a slower pH change to a physiologically acceptable range. According to the disclosure, this process can be obtained in a single step by mixing a solution with a dry combination of appropriate medicament(s) and pH adjusting agent(s).

In some embodiments, the dry pharmaceutical composition comprises one or more pharmaceutically acceptable carriers. Further provided herein are kits and systems comprising the pharmaceutical compositions as described herein. According to aspects of the invention, the dry pharmaceutical compositions have several advantages over liquid compositions, including increased stability (e.g., a long shelf life, potency and/or chiral stability) over time and upon exposure to changes in temperature.

In some aspects, the disclosure provides a pharmaceutical composition comprising a therapeutically effective amount of a dry medicament and one or more pH adjusting agents (e.g., one or more dry pH adjusting agents). In some embodiments, the pH adjusting agents are solids. In some embodiments, the pharmaceutical composition reaches a first pH after mixing with a first liquid. In some embodiments, the first pH is lower than about 7.0. In some embodiments, the first pH is lower than about 6.0. In some embodiments, the first pH is lower than about 5.0. In some embodiments, the first pH is lower than about 4.0. In some embodiments, the first pH is lower than about 3.0. In some embodiments, the first pH is lower than about 2.0. In some embodiments, the first pH is lower than about 2.2. In some embodiments, the first pH is from about 2.2 to about 5.0. In some embodiments, the first pH is lower than about 1.0. In some embodiments, the first pH is over about 7.0. In some embodiments, the first pH is over about 8.0. In some embodiments, the first pH is over about 9.0. In some embodiments, the first pH is over about 10.0. In some embodiments, the first pH is over about 11.0. In some embodiments, the first pH is over about 12.0. In some embodiments, the first pH is over about 13.0. In some embodiments, the dry medicament is more soluble in the first liquid than one or more dry pH adjusting agents. In some embodiments, the dry medicament forms a readily solubilized salt upon being mixed with the first liquid. For example, the free-base epinephrine forms a more soluble salt upon being mixed with the first liquid comprising an acid.

In some embodiments, the solution formed from the pharmaceutical composition or dry medicament and the first liquid is further contacted with one or more pH adjusting agents to reach a second pH. In certain embodiments, the second pH is a physiologically acceptable pH. In some embodiments, the second pH is a physiological pH. In some embodiments, the second pH is from about 2.2 to about 5.0 and the dry medicament is epinephrine. In some embodiments, the second pH is from about 4.2 to about 5.3 and the dry medicament is sumatriptan. In some embodiments, the second pH is from about 0.1 to about 3.0 or 9.5 to 13.5 and the dry medicament is glucagon.

In another aspect, provided herein is a medical kit comprising the pharmaceutical composition as described herein and a first liquid.

In another aspect, the disclosure provides a method of preparing a medical solution comprising mixing the pharmaceutical composition as described herein and a first liquid. In certain embodiments, the pharmaceutical composition is administered through a medical device to a subject. In certain embodiments, the pharmaceutical composition is located in a first chamber of a medical device. In certain embodiments, the first liquid is located in a second chamber of the medical device. Before injection, the pharmaceutical composition is mixed with the first liquid to dissolve the dry medicament, followed by pH adjustment by one or more dry pH adjusting agents to reach a physiologically acceptable pH. The dissolution and pH adjustment processes are generally completed within less than 5 min. In some embodiments, the dissolution and pH adjustment process are generally completed within less than about 1 min. In some embodiments, the dissolution and pH adjustment process are generally completed within less than about 30 seconds. In some embodiments, the dissolution and pH adjustment process are generally completed within less than about 10 seconds. In some embodiments, the dissolution and pH adjustment process are generally completed within less than about 5 seconds. In some embodiments the dissolution and pH adjustment process are generally completed within less than about 1 second. In certain embodiments, the medical device is an autoinjector.

In certain embodiments, the pH adjusting agent is completely separate from the dry medicament. In certain embodiments, the pH adjusting agent is of particles different from the particles of the dry medicament. In certain embodiments, the pH adjusting agent is of particles associated with the particles of the dry medicament. In certain embodiments, the pH adjusting agent is of particles within the particles of the dry medicament. In certain embodiments, the pH adjusting agent is of particles embedded in the particles of the dry medicament. In certain embodiments, the sizes of the particles of pH adjusting agent and the dry medicament are different. In certain embodiments, the sizes of the particles of pH adjusting agent and the dry medicament are similar. In certain embodiments, the pH adjusting agent dissolves slower than the dry medicament.

These and other aspects of the application are illustrated by the following non-limiting Figures and described in the Detailed Description.

BRIEF DESCRIPTION OF FIGURES

FIG. 2 shows a non-limiting embodiment of an injection system using the method as described herein.

FIG. 3 shows Table 1 of non-limiting exemplified acids in the first liquid.

FIG. 4 shows Table 2 of non-limiting exemplified pH adjusting agents.

FIG. 5 shows Table 3 of non-limiting exemplified dry medicaments and the salt forms with improved solubility after mixing with the first liquid.

FIG. 6 shows Table 4 of non-limiting exemplified reactions of the dry medicament with the first liquid and a pH adjusting agent. Specifically, the medicament forms a salt with an acid, its conjugate base, a base, or its conjugate acid to increase the solubility and the resulting exchange salt and weak acid form a solution for administration (e.g., injection). In certain embodiments, an excess amount of an acid or conjugate salt may be added to adjust final solution pH.

FIG. 7 shows non-limiting exemplified reaction types 1 and 5 with molar ratios of each components.

FIG. 8 shows additional non-limiting exemplified reaction types 1 and 5.

DETAILED DESCRIPTION

Provided herein are pharmaceutical compositions and kits comprising a therapeutic agent. Further provided herein are methods of using the pharmaceutical compositions and kits as described herein to treat or prevent a disease or condition.

In some embodiments, aspects of the invention relate to stabilizing a therapeutic agent and making it less susceptible to temperature-induced degradation, by preparing a dry pharmaceutical composition (e.g., a dry salt form) of the therapeutic agent that can be readily reconstituted (e.g., in the context of an autoinjector) for delivery to a patient.

Figure 1:
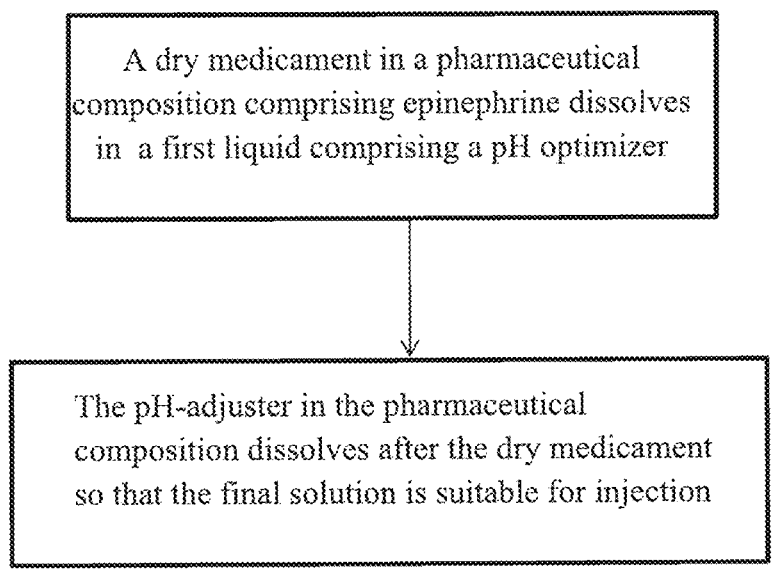
FIG. 1 illustrates a non-limiting method for a single-stage mixing and injection process.

In some aspects, the disclosure provides useful pharmaceutical compositions to store a medicament in a solid form and thus prevents its degradation. The disclosure further provides methods of preparing a medical solution from the pharmaceutical compositions as described herein. In some embodiments, a single stage mixing occurs prior to injection as illustrated by the scheme in FIG. 1. In some embodiments, upon mixing the pharmaceutical composition and the first liquid, the dry medicament dissolves faster than (e.g., before) the one or more pH adjusting agents. In some embodiments, an injection system (e.g., as illustrated in FIG. 2 or any other suitable injector/autoinjector) is used in which a dry medicament composition is kept separate from a liquid component until they are mixed prior to injection. Tables 1-3 (FIGS. 3-5) provide non-limiting examples of acids (e.g., that can be provided in liquid form), pH adjusting agents (e.g., that can be provided in solid form), and medicaments (e.g., that can be provided in solid form) that can be used. Tables 4 and 5 (e.g., FIGS. 6-8) illustrate non-limiting examples of different types of reactions that can occur involving the reagents of Tables 1-3 or other appropriate reagents. In some embodiments, the pH adjusting agent acts to adjust the pH value of the mixture from the favorable first pH for dissolving the dry medicament to the second pH proper for injection to a subject.

In some embodiments, the dry medicament generally is not very soluble in water. In certain embodiments, the dry medicament is epinephrine. In certain embodiments, the dry medicament is epinephrine of a free base form. In certain embodiments, the dry medicament is glucagon. In certain embodiments, the dry medicament is sumatriptan.

In certain embodiments, the dry medicament is not associated with the one or more pH adjusting agents. In certain embodiments, the dry medicament and the one or more pH adjusting agents are in different particles. In certain embodiments, the dry medicament is in particles that are smaller than the one or more pH adjusting agents. In certain embodiments, the dry medicament particles have a size greater than 1 nm. In certain embodiments, the dry medicament particles have a size greater than 5 nm. In certain embodiments, the dry medicament particles have a size greater than 10 nm. In certain embodiments, the dry medicament particles have a size greater than 50 nm. In certain embodiments, the dry medicament particles have a size greater than 100 nm. In certain embodiments, the dry medicament particles have a size greater than 500 nm. In certain embodiments, the dry medicament particles have a size greater than 1 µm. In certain embodiments, the dry medicament particles have a size greater than 5 µm. In certain embodiments, the dry medicament particles have a size greater than 10 µm. In some embodiments, the dry medicament particles have a size of about 20 µm to about 40 µm (e.g., about 20, 22.5, 25, 27.5, 30, 32.5, 35, or about 40 µm). In certain embodiments, the dry medicament particles have a size greater than 50 µm. In certain embodiments, the dry medicament particles have a size greater than 100 µm. In certain embodiments, the dry medicament particles have a size greater than 500 µm. In certain embodiments, the one or more pH adjusting agent particles have a size greater than 1 nm. In certain embodiments, the one or more pH adjusting agent particles have a size greater than 5 nm. In certain embodiments, the one or more pH adjusting agent particles have a size greater than 10 nm. In certain embodiments, the one or more pH adjusting agent particles have a size greater than 50 nm. In some embodiments, the one or more pH adjusting agent particles have a size of about 40 µm to about 60 µm (e.g., about 40, 45, 47.5, 50, 52.5, 55, 57.5, or about 60 µm). In certain embodiments, the one or more pH adjusting agent particles have a size greater than 100 nm. In certain embodiments the one or more pH adjusting agent particles have a size greater than 500 nm. In certain embodiments, the one or more pH adjusting agent particles have a size greater than 1 µm. In certain embodiments, the one or more pH adjusting agent particles have a size greater than 5 µm. In certain embodiments, the one or more pH adjusting agent particles have a size greater than 10 µm. In certain embodiments, the one or more pH adjusting agent particles have a size greater than 50 µm. In certain embodiments, the one or more pH adjusting agent particles have a size greater than 100 µm. In certain embodiments, the one or more pH adjusting agent particles have a size greater than 500 µm.

As used herein, numerical values of particle size refer to particle diameter as measured using known techniques (e.g., laser diffraction) and instrumentation (e.g., a size range device, for example provided by Malvern). In some embodiments, the size of a particle is representative of a population (e.g., mean, median, or average) of particles (e.g., a dry composition). In some embodiments, the dry composition comprises an amorphous solid. In some embodiments, the dry composition comprises a crystalline solid. In some embodiments, the dry composition comprises a mixture of amorphous and crystalline solids. In some embodiments, the dry composition is a solid cake. In some embodiments, the dry composition is a porous matrix.

In certain embodiments, the dry medicament is in particles that are dissolved before the one or more pH adjusting agents. In certain embodiments, the dry medicament particles dissolve faster than the one or more pH adjusting agent particles. In certain embodiments, the dry medicament is in particles that are bigger than the one or more pH adjusting agents. In certain embodiments, the dry medicament is in particles that are of similar size as the one or more pH adjusting agents. As it is to be understood, different formulations (e.g., coating, caging, etc.) of the dry medicament and the pH adjusting agents can alter the inherent solubility of these substances to achieve different dissolution rates.

In certain embodiments, the pH adjusting agent is coated with one or more layers of a pharmaceutically acceptable carrier. In certain embodiments, the pharmaceutically acceptable carrier is a solid. A pharmaceutically acceptable carrier includes any and all diluents, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

In certain embodiments, the pH adjusting agent is coated with one or more layers of a pharmaceutically acceptable polymer. In certain embodiments, the pH adjusting agent is released after dissolution of the dry medicament after mixed with the first liquid.

Figure 9A:
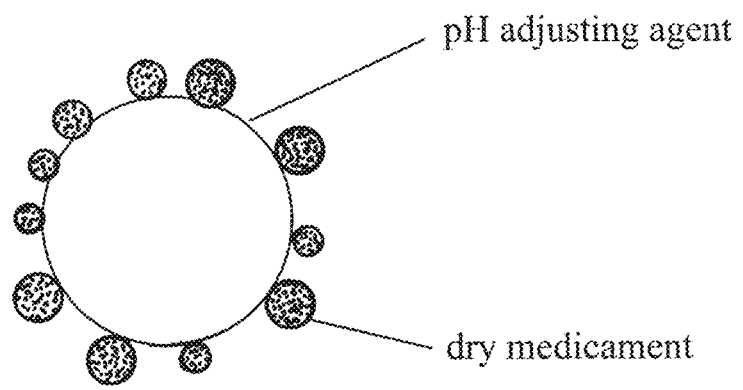
FIG. 9 shows non-limiting exemplified coatings of the pH adjusting agent with the dry medicament, wherein one or more particles of dry medicament are present on particles of pH adjusting agent (A), or the pH adjusting agent is coated with one or more layers of dry medicament (B).
Figure 9B:
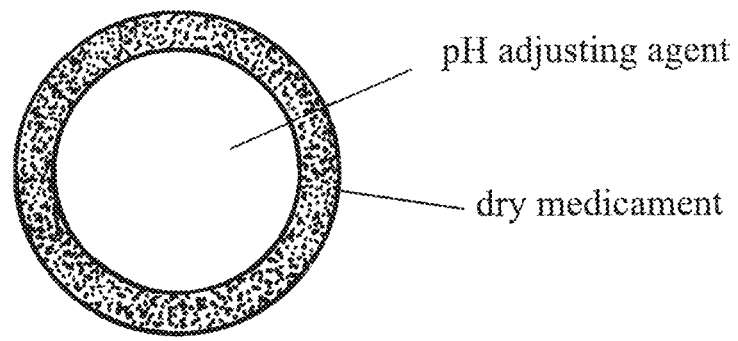

In certain embodiments, the dry medicament is associated with the pH adjusting agent (e.g., FIG. 9A). In certain embodiments, the pH adjusting agent is coated with one or more layers of the dry medicament (e.g., FIG. 9B). In certain embodiments, sodium citrate is coated with one more layers of epinephrine.

Figure 10A:
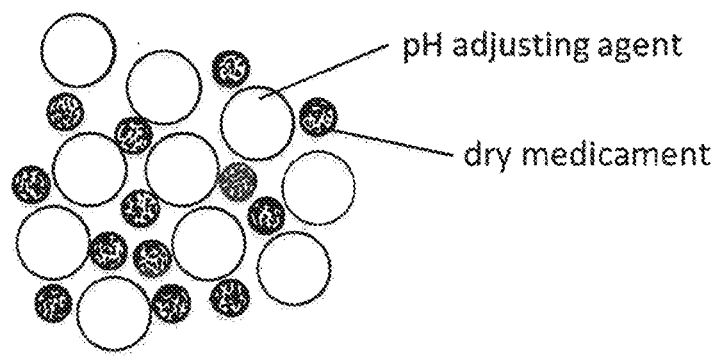
FIG. 10 depicts a non-limiting embodiment of mixtures comprising a dry medicament and a dry pH adjusting agent, wherein the medicament particle size is smaller (A) or larger (B) relative to the pH adjusting agent.
Figure 10B:
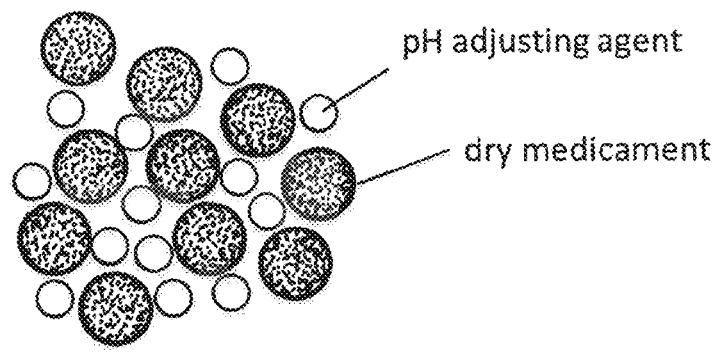

In some embodiments, the different dissolution rates of a dry medicament and a pH adjusting agent is achieved by different particle size. In some embodiments, the particle size of the dry medicament is smaller relative to the particle size of the pH adjusting agent so that the smaller medicament particle dissolves first and/or more quickly (e.g., FIG. 10A). In some embodiments, the particle size of the dry medicament is larger relative to the particle size of the pH adjusting agent (e.g., FIG. 10B). For example, in certain embodiments, the different dissolution rates of the dry medicament and the pH adjusting agent can be achieved by including a slow release coating on the pH adjusting agent. The properties of certain slow release coatings could be such that a smaller particle size provides a favorable rate of dissolution of the pH adjusting agent.

As used herein, a pH optimizing agent refers to an agent that has the capacity to optimize the pH of a solution. In certain embodiments, a pH optimizing agent facilitates dissolution of the dry medicament. In certain embodiments, the pH optimizing agent is an acid as generally described herein. In certain embodiments, the pH optimizing agent is a base as generally described herein. In certain embodiments, the pH optimizing agent is a buffer.

As used herein, a pH adjusting agent is an agent that can change the pH value of a solution. In certain embodiments, the pH adjusting agent adjusts the pH of the solution to a physiologically acceptable pH suitable for administration. In certain embodiments, the pH adjusting agent is an acid as generally described herein. In certain embodiments, the pH adjusting agent is a base as generally described herein. In certain embodiments, the pH adjusting agent is a buffer as generally described herein. In certain embodiments, the pH adjusting agent is a salt.

As generally defined herein, an acid is a chemical substance that dissociates in aqueous solution to give $H^+$. In certain embodiments, the acid is an organic acid. In certain embodiments, the acid is an inorganic acid. Examples of the acids include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, or undecylenic acid. In some embodiments, the acid is hydrochloric acid; sulfuric acid; phosphoric acid; maleic acid; 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; hydrobromic acid; hydrochloric acid; isobutyric acid; lactic acid (DL); lactobionic acid; lauric acid; maleic acid; malic acid (-L); malonic acid; mandelic acid (DL); methanesulfonic acid; naphthalene-1,5-disulfonic acid; naphthalene-2-sulfonic acid; nicotinic acid; nitric acid, oleic acid; oxalic acid; palmitic acid; pamoic acid; phosphoric acid; proprionic acid; pyroglutamic acid (-L); salicylic acid; sebacic acid; stearic acid; succinic acid; sulfuric acid; tartaric acid (+L); thiocyanic acid; toluenesulfonic acid (p); or undecylenic acid. In some embodiments, the acid is sulfuric acid, hydrochloric acid, hydrobromic acid, nitric acid, phosphoric acid, perchloric acid, formic acid, acetic acid, propionic acid, oxalic acid, maleic acid, citric acid, succinic acid, malonic acid, tartaric acid, or combinations thereof. In certain embodiments, the acid is hydrochloric acid, nitric acid, sulfuric acid, phosphoric acid, tartaric acid, malic acid, malonic acid, maleic acid, fumaric acid, succinic acid, or formic acid (e.g., FIG. 5).

As generally defined herein, a base is a chemical substance that dissociates in aqueous solution to give OH⁻. In certain embodiments, the base is an organic base. In certain embodiments, the base is an inorganic base. In certain embodiments, the base is an alkaline base. Examples of the bases include, but are not limited to, sodium citrate, sodium acetate, sodium hydroxide, potassium hydroxide, lithium hydroxide, ammonium hydroxide, calcium hydroxide, magnesium hydroxide, iron hydroxide, zinc hydroxide, copper hydroxide, manganese hydroxide, aluminum hydroxide, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, or combinations thereof. In some embodiments, the base is sodium hydroxide or potassium hydroxide.

As used herein, the term "buffer" refers to either a buffering agent or a buffering solution comprising one or more buffering agents. As generally defined herein, a buffering agent is a weak acid or base used to maintain the pH of a solution near a chosen value after the addition of another acid or base. The function of a buffering agent is to prevent a rapid change in pH when acids or bases are added to the solution. Exemplary buffering agents include but are not limited to citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof. In certain embodiments, the buffer is a sodium salt, a calcium salt, a potassium salt, or an ammonium salt. In certain embodiments, the buffer is a citrate, acetate, phosphate, sulfate, nitrate, tartrate, succinate, malate, or maleate (e.g., FIG. 4). In certain embodiments, the buffer is sodium citrate, sodium acetate, potassium hydroxide, potassium citrate, potassium acetate, sodium succinate, or potassium succinate.

As used herein, the first liquid can be a solvent or a solution. In some embodiments, the first liquid is a single solvent. In some embodiments, the first liquid is a solution comprising a pH optimizing agent and a single solvent. In some embodiments, the first liquid comprises water. In some embodiments, the first liquid comprises water and a pH optimizing agent. In some embodiments, the pH optimizing agent is an acid as generally defined herein. In some embodiments, the pH optimizing agent is HCl. In some embodiments, the first liquid is an aqueous solution comprising HCl. In some embodiments, the pH optimizing agent is a base as generally defined herein. In some embodiments, the pH optimizing agent is an alkaline base.

In some embodiments, the pH of the first liquid is from about 0.1 to about 6.9. In some embodiments, the pH of the first liquid is from about 0.5 to about 5.0. In some embodiments, the pH of the first liquid is from about 1.0 to about 5.0. In some embodiments, the pH of the first liquid is from about 2.0 to about 5.0. In one embodiment, the pH of the first liquid is from about 0.1 to about 6.0. In one embodiment, the pH of the first liquid is from about 0.1 to about 5.0. In one embodiment, the pH of the first liquid is from about 0.1 to about 4.0. In one embodiment, the pH of the first liquid is from about 0.1 to about 3.0. In one embodiment, the pH of the first liquid is from about 0.1 to about 2.0. In one embodiment, the pH of the first liquid is from about 0.1 to about 1.0. In one embodiment, the pH of the first liquid is from about 0.01 to about 2.2 and the dry medicament is epinephrine. In some embodiments, the pH of the first liquid is from about 0.25 to about 0.50. In some embodiments, the pH of the first liquid is from about 0.50 to about 0.75. In some embodiments, the pH of the first liquid is from about 0.75 to about 1.0. In some embodiments, the pH of the first liquid is from about 1.0 to about 1.25. In one embodiment, the pH of the first liquid is 1.25. In some embodiments, the pH of the first liquid is from about 1.25 to about 1.5. In some embodiments, the pH of the first liquid is from about 1.5 to about 1.75. In some embodiments, the pH of the first liquid is from about 1.75 to about 2.0. In some embodiments, the pH of the first liquid is from about 2.0 to about 2.25. In some embodiments, the pH of the first liquid is from about 2.25 to about 2.5. In some embodiments, the pH of the first liquid is from about 2.5 to about 2.75. In some embodiments, the pH of the first liquid is from about 2.75 to about 3.0.

In some embodiments, the pH of the first liquid is from about 7.0 to about 13.5. In some embodiments, the pH of the first liquid is from about 8.0 to about 13.5. In some embodiments, the pH of the first liquid is from about 9.0 to about 13.5. In some embodiments, the pH of the first liquid is from about 9.5 to about 13.5. In some embodiments, the pH of the first liquid is from about 9.5 to about 13.5 and the dry medicament is glucagon.

In some embodiments, upon mixing the pharmaceutical composition and the first liquid, the dry medicament dissolves faster than the one or more pH adjusting agents. In some embodiments, the pH adjusting agent acts to adjust the pH value of the mixture from the favorable pH for dissolving the dry medicament to the pH proper for injection in a subject (e.g., as illustrated by the reagents and reactions in FIGS. 3-8). In certain embodiments, the pH of the final solution is a physiologically acceptable pH. In some embodiments, the pH of the final solution is from about 2.2 to about 5.0 and the dry medicament is epinephrine. In some embodiments, the pH of the final solution is from about 2.2 to about 5.0 and the dry medicament is epinephrine free base form. In some embodiments, the pH of the final solution is from about 2.2 to about 5.0 and the dry medicament is epinephrine salt form. In some embodiments, the pH of the final solution is from about 2.2 to about 5.0 and the dry medicament is epinephrine hydrochloride form. In some embodiments, the pH of the final solution is from about 2.2 to about 5.0 and the dry medicament is epinephrine bitartrate form. In some embodiments, the pH of the final solution is from about 4.2 to about 5.3 and the dry medicament is sumatriptan. In some embodiments, the pH of the final solution is from about 0.1 to about 3.0 and the dry medicament is glucagon.

The dry pharmaceutical composition can be prepared from any suitable method as used in the pharmaceutical formation. For example, a drug may be chemically derived, lyophilized (freeze-dried) and/or spray dried and/or using any other technique to put the drug and/or medicament into a dry form. However, in some embodiments, it is important that the dried drug be easily and rapidly soluble so that the dry composition can be used in an autoinjector that also contains a liquid component that can be mixed with the dry drug to solubilize it upon activation of the autoinjector (e.g., immediately prior to or at the time of injection).

There are many common drug formulations that contain epinephrine in some form, including those used to treat cardiac arrest as well as anaphylaxis. Due to the insolubility of epinephrine freebase, finished dosage forms of epinephrine used in healthcare are typically formulated using an acid to form hydrochloride, bitartrate, or borate salts.

In some embodiments, the pharmaceutical composition comprising L-epinephrine freebase is placed inside a chamber of a medical device (e.g., an autoinjector). A first liquid comprising a pH optimizing agent (e.g., an acid such as HCl) is placed in another chamber. In one embodiment, the HCl solution is of 1 M or higher. In some embodiments, the HCl solution is of 0.1 M or higher. In some embodiments, the HCl solution is of 0.01 M or higher. In some embodiments, the HCl solution is of 0.001 M or higher. In some embodiments, the HCl solution is of 0.0001 M or higher. In some embodiments, the HCl solution is of 0.00001 M or higher. In some embodiments, the HCl solution is of 0.000001 M or higher.

In some embodiments, the volume of the first liquid (e.g., in an autoinjector) is about 100 µL to about 200 µL (e.g., about 100, 125, 150, 175, or about 200 µL). In some embodiments, the volume of the first liquid (e.g., in an autoinjector) is about 200 µL to about 300 µL (e.g., about 200, 225, 250, 275, or about 300 µL). In some embodiments, the volume of the first liquid (e.g., in an autoinjector) is about 300 µL to about 400 µL (e.g., about 300, 325, 350, 375, or about 400 µL). In some embodiments, the volume of the first liquid (e.g., in an autoinjector) is about 400 µL to about 500 µL (e.g., about 400, 425, 450, 475, or about 500 µL). In some embodiments, the volume of the first liquid (e.g., in an autoinjector) is about 500 µL to about 600 µL (e.g., about 500, 525, 550, 575, or about 600 µL). In some embodiments, the volume of the first liquid (e.g., in an autoinjector) is about 600 µL to about 700 µL (e.g., about 600, 625, 650, 675, or about 700 µL). In some embodiments, the volume of the first liquid (e.g., in an autoinjector) is about 700 µL to about 800 µL (e.g., about 700, 725, 750, 775, or about 800 µL). In some embodiments, the volume of the first liquid (e.g., in an autoinjector) is about 800 µL to about 1000 µL (e.g., about 800, 850, 900, 950, or about 1000 µL). In some embodiments, the volume of the first liquid (e.g., in an autoinjector) is about 1 mL to about 1.5 mL (e.g., about 1, 1.1, 1.2, 1.3, 1.4, or about 1.5 mL). In some embodiments, the liquid is of a volume greater than 1.5 mL.

In one embodiment, additional components like metabisulfite, sodium chloride and other materials may also be included in the first liquid for dissolving the therapeutic agent such as epinephrine.

In one embodiment, the epinephrine freebase is dissolved into a first liquid comprising a pH optimizing agent so the pH of the dissolved material is below a pH of 6, is below a pH of 5, is below a pH of 4, is below a pH of 3, is below a pH of 2, is between a pH of 2-5. In one embodiments, the dissolved epinephrine solution is secondly adjusted with a pH adjusting agent so the final pH is physiologically acceptable for administration.

In certain embodiments, a first solution is added to a dry composition comprising a dry medicament and a dry pH adjusting agent. In some embodiments, the first solution comprises a pH optimizing agent. In certain embodiments, the pH optimizing agent is an acid. In certain embodiments, the pH optimizing agent is a base. In certain embodiments, the pH optimizing agent is a buffer.

In certain embodiments, the dry medicament dissolves in the first solution faster than the dry pH adjusting agent. However, as the pH adjusting agent dissolves, it adjusts the pH of the resulting solution, for example to a pH range that is more physiologically acceptable than the pH of the first solution. In some embodiments, the dry pH adjusting agent is an acid. In some embodiments, the dry pH adjusting agent is a base. In some embodiments, the dry pH adjusting agent is a buffer. In certain embodiments, the buffer comprises a salt of a weak acid or a salt of a weak base, for example sodium acetate, (e.g., in dry powder form). In some embodiments, the buffer may comprise a mixture of a weak acid and its conjugate base, or a weak base and its conjugate acid (e.g., in dry powder form). In some embodiments, the buffer may comprise a mixture of citric acid and its conjugate base (e.g., in dry powder form). In some embodiments, the buffer may comprise a mixture of acetic acid and its conjugate base (e.g., in dry powder form). In some embodiments, the buffer may comprise a mixture of tartaric acid and its conjugate base (e.g., in dry powder form). In some embodiments, a buffer (e.g., in a dry powder form) for adjusting the pH of the dissolved medicament solution is already mixed with the dry medicament as described herein. However, in some embodiments, buffer (e.g., in a dry powder form) is contained inside a reservoir to receive the dissolved solution. In some embodiments, the buffer may be useful to increase the pH of the dissolved solution above a pH of 2 if a pH upon dissolution drops below a pH of 2. In some embodiments, a pH adjusting dry agent is a base. In some embodiments, the pH adjusting dry agent is sodium hydroxide. In some embodiments, the adjustment of the pH of the solution by the pH adjusting agent makes the resulting solution suitable for injection. It should be appreciated that, in some embodiments, a feature is that a medicament is being provided in an acid or a base to facilitate dissolution of the medicament and a buffer adjusts the mixture to a pH suitable for injection.

In certain embodiments, one powdered form of epinephrine, for example, is -(-) epinephrine free base. -(-) Epinephrine (epi) is poorly soluble in water. However, adding a pH optimizing agent to the aqueous solution can enhance the solubility. In certain embodiments, the addition of an acid, for example, hydrochloric acid (HCl), makes the environment more acidic thereby increasing the solubility of epinephrine.

Addition of an acid promotes faster dissolution of epinephrine. An improved dissolution rate is important if epinephrine needs to be dissolved quickly before making the injection, for example, inside an autoinjector or prefilled syringe. In certain embodiments, a fast dissolution of epinephrine is achieved by reducing the pH below about 2.2 which can be adjusted back to a pH value of about 2.2 to about 5 before injection. In one embodiment, the pH value of dissolving epinephrine is about 2.2 or below. In one embodiment, the pH value of the injection solution comprising epinephrine is about 2.2 or below. In one embodiment, the pH value of the injection solution comprising epinephrine is about 5.0 or above.

Several approaches can be employed to adjust the pH value from lower than about 2.2 to the range of about 2.2 and about 5. In some embodiments, one or more pH adjusting agents (e.g., in a dry form) are present in a dry composition containing a medicament and form a buffering system. In certain embodiments, a pH adjusting agent is a buffer. In certain embodiments, the a pH adjusting agent is buffering agent. In certain embodiments, the buffering agent is a sodium or potassium buffering agent. In certain embodiments, the buffering agent is sodium citrate or sodium acetate. In certain embodiments, the buffer system comprising trisodium citrate and citric acid.

In some embodiments, the methods provided herein allow quick dissolution of a medicament (e.g., epinephrine) inside a medical device (e.g., an autoinjector or prefilled syringe) by using a first liquid (e.g., an acidic solution) to dissolve epinephrine, followed by pH adjustment due to the slower dissolution of a pH adjusting agent (e.g., a buffer) to reach a final pH range between about 2.2 to about 5 for injection.

In some embodiments, the following reaction types are involved.

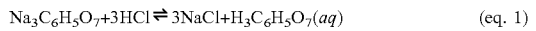

$$Na_3C_6H_5O_7 + 3HCl \rightleftharpoons 3NaCl + H_3C_6H_5O_7 (aq) \quad \text{(eq. 1)}$$

$$C_9H_{13}NO_3 + HCl \rightarrow C_9H_{13}NO_3 \cdot HCl \quad \text{(eq. 2)}$$

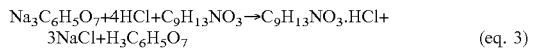

$$Na_3C_6H_5O_7 + 4HCl + C_9H_{13}NO_3 \rightarrow C_9H_{13}NO_3 \cdot HCl + 3NaCl + H_3C_6H_5O_7 \quad \text{(eq. 3)}$$

As shown in eq. 1 to eq. 3, sodium citrate and epinephrine powder react with hydrochloric acid to yield epinephrine hydrochloride and sodium chloride in a citric acid solution. Citric acid is a triprotic weak acid with three acid dissociation constants (pKa). The dissociation reactions are shown in eq. 4-eq. 6.

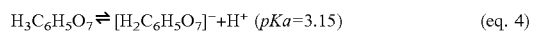

$$H_3C_6H_5O_7 \rightleftharpoons [H_2C_6H_5O_7]^- + H^+ \quad (pKa=3.15) \quad \text{(eq. 4)}$$

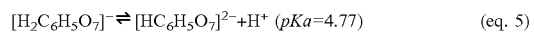

$$[H_2C_6H_5O_7]^- \rightleftharpoons [HC_6H_5O_7]^{2-} + H^+ \quad (pKa=4.77) \quad \text{(eq. 5)}$$

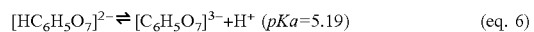

$$[HC_6H_5O_7]^{2-} \rightleftharpoons [C_6H_5O_7]^{3-} + H^+ \quad (pKa=5.19) \quad \text{(eq. 6)}$$

The pKa values of citric acid are within the pH of a target injection solution. A system comprising citric acid has a better buffer capacity and resistance to a pH drift. The combined, balanced reaction (equation 3) provides a solution with a target pH value and epinephrine concentration for injection. The pH of the solution and the concentration of sodium chloride can be adjusted by changing the relative ratio of HCl:sodium citrate and/or sodium citrate:epinephrine. In certain embodiments, the molar ratio of HCl:sodium citrate is from about 100:1 to about 1:100. In certain embodiments, the molar ratio of HCl:sodium citrate is from about 80:1 to about 1:100. In certain embodiments, the molar ratio of HCl:sodium citrate is from about 60:1 to about 1:100. In certain embodiments, the molar ratio of HCl:sodium citrate is from about 40:1 to about 1:100. In certain embodiments, the molar ratio of HCl:sodium citrate is from about 20:1 to about 1:100. In certain embodiments, the molar ratio of HCl:sodium citrate is from about 10:1 to about 1:100. In certain embodiments, the molar ratio of HCl:sodium citrate is from about 5:1 to about 1:100. In certain embodiments, the molar ratio of HCl:sodium citrate is from about 10:1 to about 1:100. In certain embodiments, the molar ratio of HCl:sodium citrate is from about 100:1 to about 1:80. In certain embodiments, the molar ratio of HCl:sodium citrate is from about 100:1 to about 1:60. In certain embodiments, the molar ratio of HCl:sodium citrate is from about 100:1 to about 1:40. In certain embodiments, the molar ratio of HCl:sodium citrate is from about 100:1 to about 1:20. In certain embodiments, the molar ratio of HCl:sodium citrate is from about 100:1 to about 1:10. In certain embodiments, the molar ratio of HCl:sodium citrate is from about 100:1 to about 1:5. In certain embodiments, the molar ratio of HCl:sodium citrate is from about 100:1 to about 1:1. In certain embodiments, the molar ratio of HCl:sodium citrate is from about 50:1 to about 1:50. In certain embodiments, the molar ratio of HCl:sodium citrate is from about 20:1 to about 1:20. In certain embodiments, the molar ratio of HCl:sodium citrate is from about 10:1 to about 1:10. In certain embodiments, the molar ratio of HCl:sodium citrate is from about 5:1 to about 1:5.

In some embodiments, both epinephrine and sodium citrate are mixed with a first liquid comprising an acid (e.g., HCl). The buffering effect can be achieved by the reversible reaction between citric acid and its conjugate base, sodium citrate (eq. 4). In certain embodiments, trisodium citrate is added to increase citrate ions in excess of HCl so as to drive the solution equilibrium to the left, thereby increasing the pH of the solution (e.g., to a range of about 2.2 to about 5.0). In some embodiments, both epinephrine and sodium acetate are mixed with a first liquid comprising an acid (e.g., HCl). In some embodiments, both epinephrine and sodium bitartrate are mixed with a first liquid comprising an acid (e.g., HCl).

In certain embodiments, provided herein is a medical device that stores a dry medicament in a first chamber and a first liquid in a second chamber. The dry powdered medicament can quickly dissolve within the first liquid followed by pH adjustment to a pH suitable for injection due to the slower dissolution of a pH adjusting agent (e.g., that is provided mixed with the medicament in a dry composition). In some embodiments, the benefits of the thermal stability of the powdered medication along with the ability to rapidly dissolve the powdered medication into a liquid dose just prior to delivery provide patients with a medicament that has much lesser storage requirements and a longer shelf life. In certain embodiments, the medical device is an autoinjector. In certain embodiments, the powdered form of epinephrine is located in the first chamber of the autoinjector and an aqueous solution comprising an acid is located in the second chamber of the autoinjector. In some embodiments, the powdered form of epinephrine is mixed with a powdered form of a pH adjusting agent (e.g., a buffer in a dry form).

In some embodiments, a dry composition comprising a dry medicament (e.g., epinephrine, glucagon, or other medicament) and a dry pH adjusting agent (e.g., citrate, acetate, or other pH adjusting agent) is provided (e.g., in an autoinjector) in a weight from about 25 mg to about 50 mg (e.g., about 25, 27.5, 30, 32.5, 35, 37.5, 40, 42.5, 45, 47.5, or about 50 mg). In some embodiments, the dry composition comprising a dry medicament (e.g., epinephrine, glucagon, or other medicament) and a dry pH adjusting agent (e.g., citrate, acetate, or other pH adjusting agent) is provided (e.g., in an autoinjector) in a weight from about 15 to about 25 mg (e.g., about 15, 16, 17, 18, 19, 20, 21, 22, 23, 24, or about 25 mg). In some embodiments, the dry composition comprising a dry medicament (e.g., epinephrine, glucagon, or other medicament) and a dry pH adjusting agent (e.g., citrate, acetate, or other pH adjusting agent) is provided (e.g., in an autoinjector) in a weight from about 5 to about 15 mg (e.g., about 5, 6, 7, 8, 9, 10, 11, 12, 13, 14, or about 15 mg). In some embodiments, the dry composition comprising a dry medicament (e.g., epinephrine, glucagon, or other medicament) and a dry pH adjusting agent (e.g., citrate, acetate, or other pH adjusting agent) is provided (e.g., in an autoinjector) in a weight from about 3 to about 5 mg (e.g., about 3, 3.25, 3.5, 3.75, 4, 4.1, 4.2, 4.3, 4.4, 4.5, 4.75, or about 5 mg). In some embodiments, the dry composition comprising a dry medicament (e.g., epinephrine, glucagon, or other medicament) and a dry pH adjusting agent (e.g., citrate, acetate, or other pH adjusting agent) is provided (e.g., in an autoinjector) in a weight from about 1 mg to about 3 mg (e.g., about 1, 1.25, 1.5, 1.75, 2, 2.1, 2.15, 2.17, 2.2, 2.3, 2.4, 2.5, 2.75, or about 3 mg). In some embodiments, the dry composition comprising a dry medicament (e.g., epinephrine, glucagon, or other medicament) and a dry pH adjusting agent (e.g., citrate, acetate, or other pH adjusting agent) is provided (e.g., in an autoinjector) in a weight from about 0.1 mg to about 1 mg (e.g., about 0.1, 0.2, 0.3, 0.4, 0.5, 0.6, 0.7, 0.8, 0.9, or about 1 mg).

In certain embodiments, provided herein is a medical device comprising a dry composition. In some embodiments, the dry composition comprises a dry medicament. In some embodiments, the dry composition comprises a dry medicament (e.g., epinephrine, glucagon, or other medicament) and a dry pH adjusting agent (e.g., citrate, acetate, or other pH adjusting agent). In some embodiments, the dry composition comprises about 1% of the dry medicament by weight and about 99% of the dry pH adjusting agent by weight. In some embodiments, the dry composition comprises about 2% of the dry medicament by weight and about 98% of the dry pH adjusting agent by weight. In some embodiments, the dry composition comprises about 3% of the dry medicament by weight and about 97% of the dry pH adjusting agent by weight. In some embodiments, the dry composition comprises about 4% of the dry medicament by weight and about 96% of the dry pH adjusting agent by weight. In some embodiments, the dry composition comprises about 5% of the dry medicament by weight and about 95% of the dry pH adjusting agent by weight. In some embodiments, the dry composition comprises about 6% of the dry medicament by weight and about 94% of the dry pH adjusting agent by weight. In some embodiments, the dry composition comprises about 7% of the dry medicament by weight and about 93% of the dry pH adjusting agent by weight. In some embodiments, the dry composition comprises about 8% of the dry medicament by weight and about 92% of the dry pH adjusting agent by weight. In some embodiments, the dry composition comprises about 9% of the dry medicament by weight and about 91% of the dry pH adjusting agent by weight. In some embodiments, the dry composition comprises about 10% of the dry medicament by weight and about 90% of the dry pH adjusting agent by weight. In some embodiments, the dry composition comprises between about 10% to about 15% of the dry medicament by weight and between about 85% to about 90% of the dry pH adjusting agent by weight. For example, about 10%, 11%, 12%, 13%, 14%, or about 15% of the dry medicament by weight and about 85%, 86%, 87%, 88%, 89%, or about 90% of the dry pH adjusting agent by weight. In some embodiments, the dry composition comprises between about 15% to about 20% of the dry medicament by weight and between about 80% to about 85% of the dry pH adjusting agent by weight. For example, about 15%, 16%, 17%, 18%, 19%, or about 20% of the dry medicament by weight and about 80%, 81%, 82%, 83%, 84%, or about 85% of the dry pH adjusting agent by weight. In some embodiments, the dry composition comprises between about 20% to about 25% of the dry medicament by weight and between about 75% to about 80% of the dry pH adjusting agent by weight. For example, about 20%, 21%, 22%, 23%, 24%, or about 25% of the dry medicament by weight and about 75%, 76%, 77%, 78%, 79%, or about 80% of the dry pH adjusting agent by weight. In some embodiments, the dry composition comprises between about 25% to about 40% of the dry medicament by weight and between about 60% to about 75% of the dry pH adjusting agent by weight. For example, about 25%, 27.5%, 30%, 32.5%, 35%, 37.5% or about 40% of the dry medicament by weight and about 60%, 62.5%, 65%, 67.5%, 70%, 72.5%, or about 80% of the dry pH adjusting agent by weight. In some embodiments, the dry composition comprises between about 40% to about 55% of the dry medicament by weight and between about 45% to about 60% of the dry pH adjusting agent by weight. For example, about 40%, 42.5%, 45%, 47.5%, 50%, 52.5% or about 55% of the dry medicament by weight and about 45%, 47.5%, 50%, 52.5%, 55%, 57.5%, or about 60% of the dry pH adjusting agent by weight. In some embodiments, the dry composition comprises between about 55% to about 70% of the dry medicament by weight and between about 30% to about 45% of the dry pH adjusting agent by weight. For example, about 55%, 57.5%, 60%, 62.5%, 65%, 67.5% or about 70% of the dry medicament by weight and about 30%, 32.5%, 35%, 37.5%, 40%, 42.5%, or about 45% of the dry pH adjusting agent by weight. In some embodiments, the dry composition comprises between about 70% to about 85% of the dry medicament by weight and between about 15% to about 30% of the dry pH adjusting agent by weight. For example, about 70%, 72.5%, 75%, 77.5%, 80%, 82.5% or about 85% of the dry medicament by weight and about 15%, 17.5%, 20%, 22.5%, 25%, 27.5%, or about 30% of the dry pH adjusting agent by weight. In some embodiments, the dry composition comprises between about 85% to about 99% of the dry medicament by weight and between about 1% to about 15% of the dry pH adjusting agent by weight. For example, about 85%, 87.5%, 90%, 92.5%, 95%, 97.5% or about 99% of the dry medicament by weight and about 1%, 2.5%, 5%, 7.5%, 10%, 12.5%, or about 15% of the dry pH adjusting agent by weight.

In some embodiments, the dry composition comprises about 1% epinephrine by weight and about 99% citrate by weight. In some embodiments, the dry composition comprises about 2% epinephrine by weight and about 98% citrate by weight. In some embodiments, the dry composition comprises about 3% epinephrine by weight and about 97% citrate by weight. In some embodiments, the dry composition comprises about 4% epinephrine by weight and about 96% citrate by weight. In some embodiments, the dry composition comprises about 5% epinephrine by weight and about 95% citrate by weight. In some embodiments, the dry composition comprises about 6% epinephrine by weight and about 94% citrate by weight. In some embodiments, the dry composition comprises about 7% epinephrine by weight and about 93% citrate by weight. In some embodiments, the dry composition comprises about 8% epinephrine by weight and about 92% citrate by weight. In some embodiments, the dry composition comprises about 9% epinephrine by weight and about 91% citrate by weight. In some embodiments, the dry composition comprises about 10% epinephrine by weight and about 90% citrate by weight. In some embodiments, the dry composition comprises between about 10% to about 15% epinephrine by weight and between about 85% to about 90% citrate by weight. For example, about 10%, 11%, 12%, 13%, 14%, or about 15% epinephrine by weight and about 85%, 86%, 87%, 88%, 89%, or about 90% citrate by weight. In some embodiments, the dry composition comprises between about 15% to about 20% epinephrine by weight and between about 80% to about 85% citrate by weight. For example, about 15%, 16%, 17%, 18%, 19%, or about 20% epinephrine by weight and about 80%, 81%, 82%, 83%, 84%, or about 85% citrate by weight. In some embodiments, the dry composition comprises between about 20% to about 25% epinephrine by weight and between about 75% to about 80% citrate by weight. For example, about 20%, 21%, 22%, 23%, 24%, or about 25% epinephrine by weight and about 75%, 76%, 77%, 78%, 79%, or about 80% citrate by weight. In some embodiments, the dry composition comprises between about 25% to about 40% epinephrine by weight and between about 60% to about 75% citrate by weight. For example, about 25%, 27.5%, 30%, 32.5%, 35%, 37.5% or about 40% epinephrine by weight and about 60%, 62.5%, 65%, 67.5%, 70%, 72.5%, or about 80% citrate by weight. In some embodiments, the dry composition comprises between about 40% to about 55% epinephrine by weight and between about 45% to about 60% citrate by weight. For example, about 40%, 42.5%, 45%, 47.5%, 50%, 52.5% or about 55% epinephrine by weight and about 45%, 47.5%, 50%, 52.5%, 55%, 57.5%, or about 60% citrate by weight. In some embodiments, the dry composition comprises between about 55% to about 70% epinephrine by weight and between about 30% to about 45% citrate by weight. For example, about 55%, 57.5%, 60%, 62.5%, 65%, 67.5% or about 70% epinephrine by weight and about 30%, 32.5%, 35%, 37.5%, 40%, 42.5%, or about 45% citrate by weight. In some embodiments, the dry composition comprises between about 70% to about 85% epinephrine by weight and between about 15% to about 30% citrate by weight. For example, about 70%, 72.5%, 75%, 77.5%, 80%, 82.5% or about 85% epinephrine by weight and about 15%, 17.5%, 20%, 22.5%, 25%, 27.5%, or about 30% citrate by weight. In some embodiments, the dry composition comprises between about 85% to about 99% epinephrine by weight and between about 1% to about 15% citrate by weight. For example, about 85%, 87.5%, 90%, 92.5%, 95%, 97.5% or about 99% epinephrine by weight and about 1%, 2.5%, 5%, 7.5%, 10%, 12.5%, or about 15% citrate by weight.

In some embodiments, the dry composition comprises about 1% glucagon by weight and about 99% citrate by weight. In some embodiments, the dry composition comprises about 2% glucagon by weight and about 98% citrate by weight. In some embodiments, the dry composition comprises about 3% glucagon by weight and about 97% citrate by weight. In some embodiments, the dry composition comprises about 4% glucagon by weight and about 96% citrate by weight. In some embodiments, the dry composition comprises about 5% glucagon by weight and about 95% citrate by weight. In some embodiments, the dry composition comprises about 6% glucagon by weight and about 94% citrate by weight. In some embodiments, the dry composition comprises about 7% glucagon by weight and about 93% citrate by weight. In some embodiments, the dry composition comprises about 8% glucagon by weight and about 92% citrate by weight. In some embodiments, the dry composition comprises about 9% glucagon by weight and about 91% citrate by weight. In some embodiments, the dry composition comprises about 10% glucagon by weight and about 90% citrate by weight. In some embodiments, the dry composition comprises between about 10% to about 15% glucagon by weight and between about 85% to about 90% citrate by weight. For example, about 10%, 11%, 12%, 13%, 14%, or about 15% glucagon by weight and about 85%, 86%, 87%, 88%, 89%, or about 90% citrate by weight. In some embodiments, the dry composition comprises between about 15% to about 20% glucagon by weight and between about 80% to about 85% citrate by weight. For example, about 15%, 16%, 17%, 18%, 19%, or about 20% glucagon by weight and about 80%, 81%, 82%, 83%, 84%, or about 85% citrate by weight. In some embodiments, the dry composition comprises between about 20% to about 25% glucagon by weight and between about 75% to about 80% citrate by weight. For example, about 20%, 21%, 22%, 23%, 24%, or about 25% glucagon by weight and about 75%, 76%, 77%, 78%, 79%, or about 80% citrate by weight. In some embodiments, the dry composition comprises between about 25% to about 40% glucagon by weight and between about 60% to about 75% citrate by weight. For example, about 25%, 27.5%, 30%, 32.5%, 35%, 37.5% or about 40% glucagon by weight and about 60%, 62.5%, 65%, 67.5%, 70%, 72.5%, or about 80% citrate by weight. In some embodiments, the dry composition comprises between about 40% to about 55% glucagon by weight and between about 45% to about 60% citrate by weight. For example, about 40%, 42.5%, 45%, 47.5%, 50%, 52.5% or about 55% glucagon by weight and about 45%, 47.5%, 50%, 52.5%, 55%, 57.5%, or about 60% citrate by weight. In some embodiments, the dry composition comprises between about 55% to about 70% glucagon by weight and between about 30% to about 45% citrate by weight. For example, about 55%, 57.5%, 60%, 62.5%, 65%, 67.5% or about 70% glucagon by weight and about 30%, 32.5%, 35%, 37.5%, 40%, 42.5%, or about 45% citrate by weight. In some embodiments, the dry composition comprises between about 70% to about 85% glucagon by weight and between about 15% to about 30% citrate by weight. For example, about 70%, 72.5%, 75%, 77.5%, 80%, 82.5% or about 85% glucagon by weight and about 15%, 17.5%, 20%, 22.5%, 25%, 27.5%, or about 30% citrate by weight. In some embodiments, the dry composition comprises between about 85% to about 99% glucagon by weight and between about 1% to about 15% citrate by weight. For example, about 85%, 87.5%, 90%, 92.5%, 95%, 97.5% or about 99% glucagon by weight and about 1%, 2.5%, 5%, 7.5%, 10%, 12.5%, or about 15% citrate by weight.

It should be appreciated that dry forms of medicaments, acids, bases, buffers, or other compounds described herein refer to one or more of a powder, a solid form, a crystalline form, pellets, particles or other dry forms of the compounds.

In some embodiments, a dry composition comprises a dry epinephrine free base. In some embodiments the dry drug composition comprises a dry L-epinephrine freebase. In some embodiments, a dry drug composition comprises a dry epinephrine salt. In some embodiments, the epinephrine salt is a maleate, malate, fumarate, acid tartrate, hydrogen tartrate, or sulfate salt of epinephrine. In some embodiments, the epinephrine salt is epinephrine hydrochloride. In some embodiments, the epinephrine salt is epinephrine bitartrate. In some embodiments, the epinephrine salt is epinephrine borate. In some embodiments, the epinephrine is L-epinephrine. In some embodiments, the dry drug composition further comprises a dry pH adjusting agent. In some embodiments, the dry drug composition further comprises a salt and/or an antioxidant. In some embodiments, the dry drug composition comprises sodium metabisulfite and/or manitol.

In some embodiments, a dry composition is prepared by drying a solution (e.g., by vacuum drying, freeze drying, lyophilizing, or any suitable drying technique, as aspects of the invention are not limited in this respect). In some embodiments the dry composition is placed inside an autoinjector as a dry powder. In some embodiments, a dry composition may have any suitable particle size that allows for efficient and rapid dissolution, solubilization, or reconstitution. In some embodiments, the particle size of the dry composition can be controlled by drying a drug solution within a confined volume. For example, in some embodiments, a drug solution is dried within the confines of an autoinjector (e.g., within one or more microfluidic channels of an autoinjector). As a result, the particle size of a dried drug composition may be on the order of the diameter of a microfluidic channel (e.g., from about 1 micron to about 500 microns in diameter). However, smaller or larger particle sizes may be used in some embodiments.

It should be appreciated that the composition can be dried to different extents depending on the conditions used and the nature of the composition (e.g., the drug and other components of the composition). In some embodiments, a dry composition has less than 50% water by weight, less than 40% water by weight, less than 30% water by weight, less than 20% water by weight, less than 10% water by weight, less than 5% water by weight, less than 1% water by weight, less than 0.1% water by weight, less than 0.01% water by weight, or less.

In some embodiments, a medicament and a pH adjusting agent are mixed in solution prior to drying into a powder form. In some embodiments, a medicament and a pH adjusting agent are dried individually. In some embodiments, the dry medicament and the dry pH adjusting agent are independently processed to achieve a desired particle size ratio using a known technique (e.g., micronization, milling, bashing, grinding).

In some embodiments, the components of a composition are weighed and measured so that the final concentration of therapeutic agent or medicament (e.g., L-epinephrine) in solution is 1 mg/mL. In one embodiment, the final concentration of therapeutic agent or medicament (e.g., L-epinephrine) is between 0.8 mg/mL and 1.2 mg/mL. In one embodiment, the final concentration of therapeutic agent or medicament (e.g., L-epinephrine) is between 0.7 mg/mL and 1.3 mg/mL. In some embodiments, the final concentration of therapeutic agent or medicament (e.g., L-epinephrine) is less than 0.8 mg/mL, for example less than 0.7 mg/mL. In some embodiments, the final concentration of therapeutic agent or medicament (e.g., L-epinephrine) is greater than 1.2 mg/mL, for example greater than 1.3 mg/mL.

In some embodiments, the concentration of one or more components (e.g., one or more acids, bases, buffers, salts, excipients, therapeutic agents, medicaments, drugs, or other components described herein) ranges from 1 nM to 1 M, for example from 1 nM to 1 µM, from 1 µm to 1 mM, from 1 mM to 10 mM, from 10 mM to 100 mM, from 100 mM to 500 mM, from 500 mM to 1 M, about 1 mM, about 5 mM, about 10 mM, about 50 mM, about 100 mM, about 500 mM, about 1 M, or higher or lower depending on the component and/or the application (e.g., in the final solution after dissolution).

A non-limiting example of an injection system (e.g., syringe/autoinjector device) is shown in FIG. 2. Injection system 20 has a syringe 40 (e.g., for holding a liquid component) and a mixer 22 (e.g., for holding a dry medicament composition). Syringe 40 has a cylindrical tube 42 defining a volume. Cylindrical tube 42 of the syringe 40 tapers down to an outlet port 48. Syringe 40 has a plunger 50 with a depressing handle 52, a shaft 54, and a piston 56 for forcing liquid component 26 out of the outlet port 48. Injector 30 is shown as a needle 60 as a part of mixer 22 although it can be separate from the mixer 22. The injector 30 can also be a nozzle or tubing for delivery of the mixed combined medicament 28. Mixer 22 is illustrated with a housing 64 that defines an interior flow chamber 66 with an inlet 68 and an outlet 70. A mixer 22 with a single channel, such as a microchannel 124, is shown. In this embodiment, micro-channel 124 of mixing device 22 is a serpentine channel, which defines a fluid pathway between the inlet 68 and the outlet 70. Fluid may enter in and out of the outlet 70 as well as the inlet 68. Serpentine channel 124 has two functions: the first function enables miniaturization of the channel structure by bending the fluid flow direction so that the channel can double back, thus a longer channel more efficiently utilizes a smaller area. The second function is that the natural flow becomes disrupted every time there is a bend or elbow in the channel, which results in mixing dependent on the cross section of the channel. In certain embodiments, liquid is pushed through the mixer 22 and out of the needle 60. In some embodiments, outlet port 48 is connected to inlet 68 and fluid from syringe 40 is pushed through the dry medicament in mixer 22, thereby dissolving, solubilizing, and/or reconstituting the dry medicament. In some embodiments, the dry medicament is separated from the liquid by a configuration (e.g., comprising a seal, a membrane, one or more valves, or other systems, or any combination thereof) that keeps the dry medicament dry until it is mixed with the liquid (e.g., by rupturing or piercing a seal or membrane and/or opening one or more valves to connect the liquid component to the dry medicament composition) prior to injection into the subject. The system illustrated in FIG. 2 is non-limiting and compositions described herein can be used in connection with any suitable injection system (e.g., a system wherein a dry medicament composition, for example comprising a medicament and a pH adjusting agent, is separated from a liquid component, and wherein the liquid component and the dry medicament composition are mixed prior to injection). In some embodiments, an injection system comprises one or more features for increasing the physical mixing of the medicament composition and the liquid component in order to promote dissolution. However, in some embodiments sufficient mixing occurs when the liquid component is contacted to the dry medicament composition.

In certain embodiments, a powdered medicament comprising epinephrine and at least one powdered pH adjusting agent (e.g., a buffer) are located in a first chamber of the syringe/autoinjector device. In certain embodiments, the buffer is sodium citrate, sodium acetate, potassium citrate, potassium acetate, sodium succinate, or potassium succinate. In some embodiments, the first liquid comprising a solvent (e.g., water) and a pH optimizing agent (e.g., an acid) is located in a second chamber. In some embodiments, the pH optimizing agent is HCl.

Before administration, the pharmaceutical composition in the first chamber of the medical device is contacted with the first fluid in the second chamber to generate a solution for injection. In certain embodiments, the contact is carried out in the first chamber. In certain embodiments, the contact is carried out in a second chamber. In certain embodiments, the contact is carried out in a third chamber. In certain embodiments, the pharmaceutical composition and the first fluid mix partially. In certain embodiments, the pharmaceutical composition and the first fluid completely mix to generate a solution. In certain embodiments, epinephrine is located in the first chamber and contacted with an acidic first fluid from the second chamber at a pH of about 2.2 or lower. In certain embodiments, the dissolution of epinephrine in the first liquid is followed by a release of a pH adjusting agent to bring the final pH of about 2.2 to about 5.0.

In some embodiments, the different dissolution rates of epinephrine and the pH adjusting agent is achieved by different particle size. In some embodiments, the particle size of epinephrine is smaller relative to the particle size of the pH adjusting agent so that the smaller epinephrine particle is more likely to dissolve first, and/or more quickly, while the pH is initially lower than 2.2, and the pH adjusting agent, with the larger particle size, dissolves more slowly causing the pH of the combined solution to then increase into a target range of about 2.2 to about 5.0.

The pharmaceutical composition provided herein can be administered by a parenteral, intravenous, intramuscular, or subcutaneous route. In certain embodiments, the route of administration is subcutaneous. In certain embodiments, the route of administrate is intravenous.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Also encompassed by the disclosure are kits (e.g., pharmaceutical packs). The inventive kits may be useful for preventing and/or treating a disease or condition (e.g., an allergy reaction). The kits provided may comprise an inventive pharmaceutical composition and a container (e.g., a vial, ampule, bottle, syringe, and/or dispenser package, or other suitable container). The kits provided may comprise an inventive pharmaceutical composition in a medical device (e.g., an autoinjector). In certain embodiments, the kits further include instructions for administering the composition.

In certain embodiments, the therapeutic agent is selected from the group consisting of Agrylin (anagrelide HCl), Akten (lidocaine hydrochloride), Apokyn (apomorphine hydrochloride), Arestin (minocycline hydrochloride), Avandamet (rosiglitazone maleate and metformin HCl), Avelox I.V. (moxifloxacin hydrochloride), Cardizem® (Diltiazem HCl for injection), Contrave (naltrexone HCl and bupropion HCl), Gemzar (gemcitabine HCL), Hycamtin (topotecan hydrochloride), Lamisil (terbinafine hydrochloride), Metozolv ODT (metoclopramide hydrochloride), Namenda (memantine HCl), Paxil (paroxetine hydrochloride), Oxecta (oxycodone HCl), Quillivant XR (methylphenidate hydrochloride), Redux (dexfenfluramine hydrochloride), Relpax (eletriptan hydrobromide), Reminyl (galantamine hydrobromide), Renagel (sevelamer hydrochloride), Requip (ropinirole hydrochloride), Ritalin LA (methylphenidate HCl), Savella (milnacipran hydrochloride), Strattera (atomoxetine HCl), Tasigna (nilotinib hydrochloride monohydrate), Tiazac (diltiazem hydrochloride), Valcyte (valganciclovir HCl), Valtrex (valacyclovir HCl), VERSED (midazolam HCl), Zanaflex (tizanidine hydrochloride), Zingo (lidocaine hydrochloride monohydrate), Ziprasidone (ziprasidone hydrochloride), Zoloft (sertraline HCl), Zometa (zoledronic acid), Zyrtec (cetirizine HCl), glucagon, or sumatriptan.

Pharmaceutically acceptable excipients include any and all diluents, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

The provided medical solution can be delivered by intradermal, intramuscular, intranasal, intravenous, oral, rectal, subcutaneous, topical, or vaginal administration. In certain embodiments, the provided medical solution is administered intradermally or intramuscularly. Suitable devices for use in delivering intradermal or intramuscular medical solution described herein include conventional syringes or short needle devices such as those described in U.S. Pat. Nos. 4,886,499; 5,190,521; 5,328,483; 5,527,288; 4,270,537; 5,015,235; 5,141,496; and 5,417,662.

In some embodiments, the amount of a therapeutic agent in the medical solution is an effective amount sufficient to elicit the desired biological response, i.e., treat the condition. In some embodiments, the amount of a therapeutic agent in the medical solution is a therapeutically effective amount sufficient to provide a therapeutic benefit in the treatment of a condition or to delay or minimize one or more symptoms associated with the condition. The term "therapeutically effective amount" can encompass an amount that improves overall therapy, reduces or avoids symptoms or causes of the condition, or enhances the therapeutic efficacy of another therapeutic agent. In some embodiments, the effective amount is a prophylactically effective amount sufficient to prevent a condition, or one or more symptoms associated with the condition or prevent its recurrence.

As used herein, the effective amount of a therapeutic agent will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In some embodiments, the medical solution is administered to a human subject. In some embodiments, the medical solution is administered to a non-human subject.

In certain embodiments, the dry medicaments or pharmaceutical compositions as described herein are stable upon changes of temperature. In some embodiments, a dry composition described herein and/or exemplified in the Examples retains greater than 90% potency, greater than 95% potency, between 90% and 100% potency, or between 90% and 115% potency when subjected to the following temperature exposure of less than –30° C., or between –30° C. and –25° C., or less than –25° C., or between –25° C. and –20° C., or less than –20° C., or between –20° C. and –15° C., or less than –15° C., or between –15° C. and –10° C., or less than –10° C., or between –10° C. and –5° C., or less than –5° C., or between –5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In some embodiments, after the L-epinephrine powder has been dissolved in an injector device, the resulting solution retains a potency greater than 90% potency, greater than 95% potency, between 90% and 100% potency, or between 90% and 115% potency even when the dry L-Epinephrine has been previously subject to a temperature exposure of less than –30° C., or between –30° C. and –25° C., or less than –25° C., or between –25° C. and –20° C., or less than –20° C., or between –20° C. and –15° C., or less than –15° C., or between –15° C. and –10° C., or less than –10° C., or between –10° C. and –5° C., or less than –5° C., or between –5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In certain embodiments, the dry medicaments or pharmaceutical compositions as described herein comprise a chiral therapeutic agent. In certain embodiments, the dry medicaments or pharmaceutical compositions as described herein comprise a chiral L-Epinephrine. In some embodiments, a dry pharmaceutical composition described herein retains a chiral purity greater than 60%, greater than 70%, greater than 75%, greater than 80%, greater than 85%, greater than 90%, greater than 95%, 95% to 100%, L-Epinephrine when subject to a temperature exposure of less than –30° C., or between –30° C. and –25° C., or less than –25° C., or between –25° C. and –20° C., or less than –20° C., or between –20° C. and –15° C., or less than –15° C., or between –15° C. and –10° C., or less than –10° C., or between –10° C. and –5° C., or less than –5° C., or between –5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In some embodiments, after the L-epinephrine powder has been dissolved in an injector device, the resulting solution retains a chiral purity greater than 60%, greater than 70%, greater than 75%, greater than 80%, greater than 85%, greater than 90%, greater than 95%, 95% to 100%, even when the dry L-Epinephrine has been previously subject to a temperature exposure of less than –30° C., or between –30° C. and –25° C., or less than –25° C., or between –25° C. and –20° C., or less than –20° C., or between –20° C. and –15° C., or less than –15° C., or between –15° C. and –10° C., or less than –10° C., or between –10° C. and –5° C., or less than –5° C., or between –5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20°

C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:

1. An autoinjector comprising a dry pharmaceutical composition that comprises a mixture of a therapeutically effective amount of a dry epinephrine and one or more dry pH adjusting agents, wherein the dry epinephrine and one or more dry pH adjusting agents are located in a first chamber of the autoinjector, wherein the autoinjector comprises a second chamber comprising a first liquid, and wherein the first liquid is an acid aqueous solution having a pH from 0.1 to 6.0, wherein the dry epinephrine and the one or more dry pH adjusting agents are in different particles, and wherein the dry epinephrine particles dissolve faster than the one or more dry pH adjusting agent particles when mixed with the first liquid.

2. The autoinjector of claim 1, wherein the dry epinephrine is more soluble in the acid than the one or more dry pH adjusting agents.

3. The autoinjector of claim 1, wherein the dry epinephrine is in particles that are smaller than the one or more dry pH adjusting agents.

4. The autoinjector of claim 3, wherein the dry epinephrine particles have a size between about 1 µm and about 30 µm.

5. The autoinjector of claim 3, wherein the one or more dry pH adjusting agent particles have a size between about 35 µm and about 100 µm.

6. The autoinjector of claim 1, wherein the one or more dry pH adjusting agents are coated with one or more layers of a pharmaceutically acceptable carrier or one or more layers of a pharmaceutically acceptable polymer.

7. The autoinjector of claim 1, wherein the first liquid is an acid, and the acid is HCl, phosphoric acid, or sulfuric acid.

8. The autoinjector of claim 1, wherein the dry epinephrine is soluble at pH of about 0.5 to 6.9.

9. The autoinjector of claim 1, wherein the one or more dry pH adjusting agents are selected from the group consisting of sodium and potassium buffering agents.

10. The autoinjector of claim 1, wherein the dry epinephrine is epinephrine of a free base form.

11. The autoinjector of claim 1, wherein the one or more dry pH adjusting agents comprise sodium citrate.

12. The autoinjector of claim 1, wherein the dry epinephrine is between 5 to 10% by weight of the dry pharmaceutical composition and the one or more dry pH adjusting agents are between 90 to 95% by weight of the dry pharmaceutical composition.

13. The autoinjector of claim 1, wherein the acid comprises HCl at a pH of between 0.5 and 2.0.

14. The autoinjector of claim 1, wherein the composition is an amorphous solid or a porous matrix.

15. A method of preparing an epinephrine solution comprising mixing the dry pharmaceutical composition and the first liquid within the autoinjector of claim 1.

16. The method of claim 15, wherein the first liquid is sterile.

17. The method of claim 15, wherein the first liquid comprises one solvent.

18. The method of claim 17, wherein the first liquid comprises water.

19. The method of claim 15, wherein the pH adjusting agent is sodium citrate, sodium acetate, potassium citrate, or potassium acetate.

20. The method of claim 15, wherein the first liquid comprises water and an acid.

21. The method of claim 15, wherein the dry epinephrine forms a readily solubilized salt upon being mixed with the first liquid.

* * * * *